United States Patent
Koshio et al.

(10) Patent No.: US 7,056,910 B2
(45) Date of Patent: Jun. 6, 2006

(54) 1,4,5,6-TETRAHYDROIMIDAZO[4,5-D] DIAZEPINE DERIVATIVES OR SALTS THEREOF

(75) Inventors: Hiroyuki Koshio, Tsukuba (JP); Akio Kakefuda, Tsukuba (JP); Ippei Sato, Tsukuba (JP); Ryutaro Wakayama, Tsukuba (JP); Masanao Sanagi, Tsukuba (JP)

(73) Assignee: Astellas Pharma Inc., Tokyo (JP)

( * ) Notice: Subject to any disclaimer, the term of this patent is extended or adjusted under 35 U.S.C. 154(b) by 325 days.

(21) Appl. No.: 10/432,732

(22) PCT Filed: Nov. 27, 2001

(86) PCT No.: PCT/JP01/10328

§ 371 (c)(1),
(2), (4) Date: May 27, 2003

(87) PCT Pub. No.: WO02/44179

PCT Pub. Date: Jun. 6, 2002

(65) Prior Publication Data

US 2004/0034012 A1 Feb. 19, 2004

(30) Foreign Application Priority Data

Nov. 28, 2000 (JP) .............................. 2000-360809

(51) Int. Cl.
*A61P 9/00* (2006.01)
*A61K 31/55* (2006.01)
*A07D 487/00* (2006.01)

(52) U.S. Cl. ...................................... 514/215; 540/578

(58) Field of Classification Search ................ 514/215; 540/578
See application file for complete search history.

(56) References Cited

U.S. PATENT DOCUMENTS

| | | | |
|---|---|---|---|
| 5,225,402 A | 7/1993 | Ogawa et al. | 514/23 |
| 5,258,510 A | 11/1993 | Ogawa et al. | 540/476 |
| 5,338,755 A | 8/1994 | Wagnon et al. | 514/414 |
| 5,397,801 A | 3/1995 | Wagnon et al. | 514/418 |
| 5,436,254 A | 7/1995 | Ogawa et al. | 514/312 |
| 5,481,005 A | 1/1996 | Wagnon et al. | 548/537 |
| 5,559,230 A | 9/1996 | Ogawa et al. | 540/569 |
| 5,578,633 A | 11/1996 | Wagnon et al. | 514/418 |
| 5,652,247 A | 7/1997 | Ogawa et al. | 514/314 |
| 5,710,150 A | 1/1998 | Taniguchi et al. | 514/211.15 |
| 5,723,606 A | 3/1998 | Tanaka et al. | 540/578 |
| 5,856,564 A | 1/1999 | Tanaka et al. | 540/450 |
| 5,985,869 A | 11/1999 | Ogawa et al. | 514/221 |
| 5,994,350 A | 11/1999 | Foulon et al. | 514/232.8 |
| 6,046,341 A | 4/2000 | Foulon et al. | 548/411 |

FOREIGN PATENT DOCUMENTS

| | | |
|---|---|---|
| EP | 0 346 068 | 6/1989 |
| EP | 0 382 185 | 6/1994 |
| WO | WO 91/05549 | 5/1991 |
| WO | WO 93/03013 | 2/1993 |
| WO | WO 95/06035 | 3/1995 |
| WO | WO 97/01556 | 1/1997 |

*Primary Examiner*—Brenda Coleman
(74) *Attorney, Agent, or Firm*—Finnegan, Henderson, Farabow, Garrett & Dunner, L.L.P.

(57) ABSTRACT

To provide a compound having a superior arginine vasopressin antagonism. A novel 1,4,5,6-tetrahydroimidazo[4,5-d]benzazepine derivative or a pharmaceutically acceptable salt thereof.

7 Claims, No Drawings

1,4,5.6-TETRAHYDROIMIDAZO[4,5-D] DIAZEPINE DERIVATIVES OR SALTS THEREOF

This application is the National Stage of International Application No. PCT/JP01/10328, filed Nov. 27, 2001.

TECHNICAL FIELD

The present invention relates to a novel 1,4,5,6-tetrahydroimidzo[4,5-d]benzazepine derivative or a salt thereof useful as a drug, especially an arginine vasopressin receptor antagonist and to a drug comprising the compound as an active ingredient.

BACKGROUND ART

Arginine vasopressin (AVP) is an antidiuretic hormone of a peptide comprising 9 amino acids as biosynthesized and secreted in a hypothalamohypophysial system and is known to have an action to promote water reabsorption in a kidney distal uriniferous tubule, contract a blood vessel and elevate a blood pressure and to act as a neurotransmitter, etc. in a brain.

As a receptor of AVP, there are known three kinds of subtypes of $V_{1A}$, $V_{1B}$ and $V_2$. An AVP receptor antagonist to competitively inhibit the binding to the $V_{1A}$ and/or $V_2$ receptor of AVP is expected as a drug for suppressing contraction of a vascular smooth muscle and suppressing pressure rise or as a drug for suppressing water reabsorption in a kidney collecting tubule, or as a drug having a combination of these actions (see NIPPONRINSHO, Vol. 58, Special Issue, "Hypertension (the Last Volume)", pp. 292–296 (2000)).

On the other hand, with the diversification of medical treatment and the age advance, it has become uncommon to use a drug singly, and in the most case, a plurality of drugs are administered simultaneously or while shifting the administration time. This is also applicable in the field of the AVP receptor antagonist. The drug is inactivated in a liver due to the action of drug metabolizing enzymes and converted into a metabolite. Among these drug metabolizing enzymes, cytochrome P450 (CYP) is the most important. CYP includes many molecular species. When a plurality of drugs metabolized from CYP of the same molecular species compete on the metabolizing enzyme thereof, it is considered that the drug receives some metabolic inhibition depending on the affinity of the drug with CYP. As a result, drug interactions such as rise of concentration in blood and prolongation of half-life in blood are revealed.

Such drug interactions are not preferred except the case where the drug is used with the intention of revealing an additive action or potentiation, and there may be the case where an unexpected side effect is revealed. Accordingly it is demanded to create a drug having a low affinity with CYP and a little possibility of the drug interaction.

Hitherto, as the foregoing AVP receptor antagonist, compounds of a peptide type and compounds of a non-peptide type have been synthesized (see, for example, JP-A-2-32098, WO 91/05549, EP0382185, WO 93/03013, WO 95/03305, WO 95/06035, and WO 97/15556).

Among them, WO 95/03305 discloses that a condensed benzazepine derivative represented by the following general formula or its salt is useful as an AVP receptor antagonist.

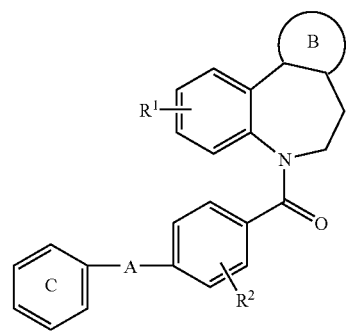

(In the formula, the symbols are as defined in the patent document.)

That is, this patent document describes some condensed benzazepine derivatives and salts thereof but does not disclose at all the compounds of the invention, wherein the ring B represents an optionally substituted nitrogen-containing aromatic 5-membered ring having at least one nitrogen atom and further optionally having one oxygen or sulfur atom; $R^1$ represents a hydrogen atom; A represents —NHCO—$(CR^3R^4)_n$—; n is 0; and the ring C represents an optionally substituted benzene ring. Further, this patent document describes the $V_1$ and/or $V_2$ receptor antagonism of AVP but does not mention the inhibition activity against the drug metabolizing enzyme CYP.

As described previously, as the AVP receptor antagonist, the compounds as described in the above-cited patent documents are known. But, it is an important problem from the standpoint of medical treatment to create a more superior AVP receptor antagonist and to create an AVP receptor antagonist free from side effects based on the inhibition of the drug metabolizing enzyme CYP.

DISCLOSURE OF THE INVENTION

The present inventors further made extensive and intensive investigations with respect to compounds having an antagonism against the AVP receptor. As a result, it has been found that a novel 1,4,5,6-tetrahydroimidazo[4,5-d]benzazepine derivative of the invention has a superior antagonism against the AVP receptor and has a lower inhibition activity against the drug metabolizing enzyme CYP3A4, leading to accomplishment of the invention.

Specifically, according to the invention, there is provided a novel 1,4,5,6-tetrahydroimidazo[4,5-d]benzazepine derivative represented by the following general formula (I) or a pharmaceutically acceptable salt thereof, which is useful as an AVP receptor antagonist.

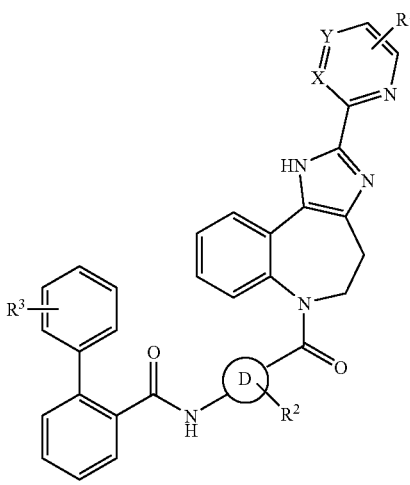

(In the formula, the ring D represents phenylene or pyridinediyl; X and Y may be the same or different and each represents CH or N; and $R^1$, $R^2$ and $R^3$ may be the same or different and each represents a hydrogen atom, a hydroxyl group, a halogen, or a lower alkyl, hereinafter the same.)

Compounds represented by the foregoing general formula (I), wherein the ring D represents 1,4-phenylene, pyridine-2,5-diyl, or pyridine-3,6-diyl, or pharmaceutically acceptable salts thereof are preferable. Compounds represented by the foregoing general formula (I), wherein the ring D represents 1,4-phenylene, pyridine-2,5-diyl, or pyridine-3, 6-diyl; X and Y each represents CH; and $R^1$ represents a hydrogen atom, or pharmaceutically acceptable salts thereof are more preferable. Compounds represented by the foregoing general formula (I), wherein the ring D represents 1,4-phenylene; X and Y each represents CH; $R^1$ represents a hydrogen atom; and $R^2$ and $R^3$ each represents a hydrogen atom, or pharmaceutically acceptable salts thereof are the most preferable.

Particularly preferred examples of the compounds include:
  N-{4-[2-(2-pyridyl)-1,4,5,6-tetrahydroimidazo[4,5-d][1]benzazepine-6-carbonyl]phenyl}biphenyl-2-carboxamide,
  N-{3-fluoro-4-[2-(2-pyridyl)-1,4,5,6-tetrahydroimidazo[4,5-d][1]benzazepine-6-carbonyl]phenyl}biphenyl-2-carboxamide,
  2'-fluoro-N-{4-[2-(2-pyridyl)-1,4,5,6-tetrahydroimidazo[4,5-d][1]benzazepine-6-carbonyl]phenyl}biphenyl-2-carboxamide,
  N-{5-[2-(2-pyridyl)-1,4,5,6-tetrahydroimidazo[4,5-d][1]benzazepine-6-carbonyl]-2-pyridyl}biphenyl-2-carboxamide,
  N-{6-[2-(2-pyridyl)-1,4,5,6-tetrahydroimidazo[4,5-d][1]benzazepine-6-carbonyl]-3-pyridyl}biphenyl-2-carboxamide,
  N-{2-hydroxy-4-[2-(2-pyridyl)-1,4,5,6-tetrahydroimidazo[4,5-d][1]benzazepine-6-carbonyl]phenyl}biphenyl-2-carboxamide, and
  pharmaceutically acceptable salts thereof.

The 1,4,5,6-tetrahydroimidazo[4,5-d]benzazepine derivative having an antagonism against the AVP receptor according to the invention is structurally characterized in that a 6-membered aromatic ring having nitrogen at the 2-position thereof is substituted at the 2-position of the imidazobenzazepine ring. Such a structural characteristic achieves a reduction of the affinity with the drug metabolizing enzyme CYP3A4.

Further, according to the invention, there is provided a pharmaceutical composition comprising, as an active ingredient, a 1,4,5,6-tetrahydroimidazo[4,5-d]benzazepine derivative represented by the foregoing general formula (I) or a pharmaceutically acceptable salt thereof. Concretely, the invention provides a pharmaceutical composition as an arginine vasopressin receptor antagonist, which comprises, as an active ingredient, a 1,4,5,6-tetrahydroimidazo[4,5-d]benzazepine derivative represented by the foregoing general formula (I) or a pharmaceutically acceptable salt thereof.

Moreover, according to the invention, there is provided a therapeutic drug for heart failure or a therapeutic drug for hyponatremia, which comprises, as an active ingredient, a 1,4,5,6-tetrahydroimidazo[4,5-d]benzazepine derivative represented by the foregoing general formula (I); a compound represented by the foregoing general formula (I), wherein the ring D represents 1,4-phenylene, pyridine-2,5-diyl, or pyridine-3,6-diyl; a compound represented by the foregoing general formula (I), wherein the ring D represents 1,4-phenylene, pyridine-2,5-diyl, or pyridine-3,6-diyl, X and Y each represents CH, and $R^1$ represents a hydrogen atom; a compound represented by the foregoing general formula (I), wherein the ring D represents 1,4-phenylene, X and Y each represents CH, $R^1$ represents a hydrogen atom, and $R^2$ and $R^3$ each represents a hydrogen atom;

N-{4-[2-(2-pyridyl)-1,4,5,6-tetrahydroimidazo[4,5-d][1]benzazepine- 6-carbonyl]phenyl}biphenyl-2-carboxamide;

N-[3-fluoro-4-[2-(2-pyridyl)-1,4,5,6-tetrahydroimidazo[4,5-d][1]benzazepine-6-carbonyl]phenyl]biphenyl-2-carboxamide;

2'-fluoro-N-{4-[2-(2-pyridyl)-1,4,5,6-tetrahydroimidazo[4,5-d][1]benzazepine-6-carbonyl]phenyl}biphenyl-2-carboxamide;

N-{5-[2-(2-pyridyl)-1,4,5,6-tetrahydroimidazo[4,5-d][1]benzazepine-6-carbonyl]-2-pyridyl}biphenyl-2-carboxamide;

N-{6-[2-(2-pyridyl)-1,4,5,6-tetrahydroimidazo[4,5-d][1]benzazepine-6-carbonyl]-3-pyridyl}biphenyl-2-carboxamide;

N-{2-hydroxy-4-[2-(2-pyridyl)-1,4,5,6-tetrahydroimidazo[4,5-d][1]benzazepine-6-carbonyl]phenyl}biphenyl-2-carboxamide; or a pharmaceutically acceptable salt thereof.

The compounds of the invention will be further described below.

In this description, the term "lower alkyl" means a linear or branched carbon chain having from 1 to 6 carbon atoms ($C_{1-6}$), and specific examples include methyl, ethyl, propyl, isopropyl, butyl, tert-butyl, pentyl, neopentyl, and hexyl. Of these are preferable $C_{1-3}$ alkyls including methyl, ethyl and isopropyl, with methyl and ethyl being particularly preferred.

Examples of the "halogen" include a fluorine atom, a chlorine atom, a bromine atom, and an iodine atom.

Each of the foregoing substituents $R^1$, $R^2$ and $R^3$ may be bound to any position of each ring, but it is desired that $R^3$ is bound to the ortho- or para-position.

The compounds represented by the general formula (I) may possibly have an asymmetric carbon atom depending on the kind of the substituent(s), and optical isomers may be present based on this. The invention includes all of mixtures or isolated compounds of these optical isomers.

Further, with respect to the compounds of the invention, position isomers based on the imidazole fused on the benzazepine ring may be considered. The invention includes all of mixtures or isolated compounds of these position isomers.

Moreover, the compounds of the invention may possibly form an acid-addition salt. The invention includes such a salt so far as they are a pharmaceutically acceptable salt. Specifically, examples include acid addition salts of an inorganic acid such as hydrochloric acid, hydrobromic acid, hydroiodic acid, sulfuric acid, nitric acid, and phosphoric acid; and acid addition salts of an organic acid such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, p-toluenesulfonic acid, aspartic acid, and glutamic acid. In addition, the invention includes various hydrates, solvates and crystal polymorphisms of the compound of the invention and its pharmaceutically acceptable salt. Incidentally, the compound of the invention includes all of so-called prodrugs, i.e., compounds that will be metabolized and converted into the compound of the foregoing general formula (I) or its salt within a living body. As the group to form the prodrug according to the invention are enumerated those groups described in *Prog Med.*, 5, 2157–2161 (1985) and *Iyakuhin No Kaihatsu* (Development of Drugs), Vol. 7, "Molecular Design", 163–198 (1990), by Hirokawa Publishing Co.

Production Process

The compound of the invention and its pharmaceutically acceptable salt can be produced through application of various known synthesis processes by utilizing the characteristic features based on the basic skeleton thereof or kinds of the substituents. Representative production processes will be enumerated below. Incidentally, in some case, it is effective on the production technology that depending on the kind of a functional group, the functional group is replaced by a protective group, i.e., a group that can be readily converted into the functional group in the state of the starting materials or intermediates. Thereafter, if desired, the protective group is removed, thereby enabling to obtain the desired compound. Examples of such a functional group include a hydroxyl group and a carboxyl group. Examples of the protective group thereof include the protective groups as described in Greene and Wuts, *Protective Groups in Organic Synthesis (third edition)*, and these may be properly used depending on the reaction condition.

Further, as other process, a process in which in a benzyl ether protected material of a hydroxyl group, pentamethylbenzene is applied in a strongly acidic solution such as trifluoroacetic acid, thereby undergoing deprotection can be enumerated.

(First Production Process)

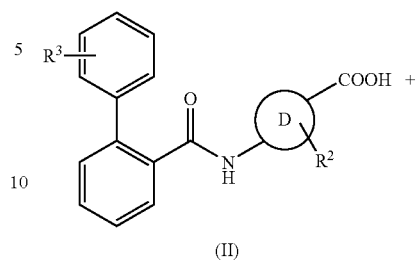

(II)
or its reative derivative

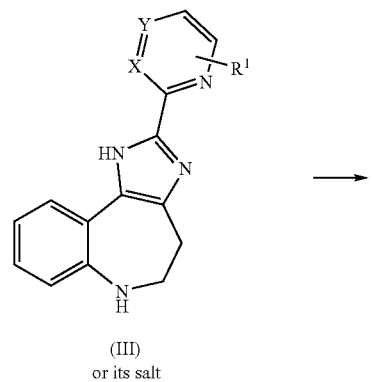

(III)
or its salt

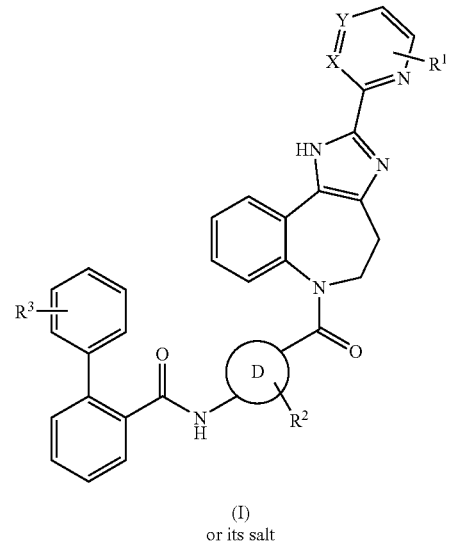

(I)
or its salt

This production process is a process in which an optionally protected substituted aromatic carboxylic acid represented by the formula (II) or its reactive derivative and an optionally protected benzazepine derivative represented by the formula (III) or its salt are subjected to amidation in an ordinary manner, and the protective group(s) is removed, if desired, to produce the compound (I) of the invention.

Examples of the reactive derivative of the compound (II) include usual esters such as methyl esters, ethyl esters, and tert-butyl esters; acid halides such as acid chlorides and acid bromides; acid azides; active esters with N-hydroxybenzotriazole, p-nitrophenol, N-hydroxysuccimide, etc.; symmetric acid anhydrides; and mixed acid anhydrides with an alkyl carbonate, p-toluenesufonic acid, etc.

Further, when the compound (II) is reacted in a liberated acid or reacted without isolating the active ester, it is suitable to use a condensing agent such as dicyclohexylcarbodiimide, carbonyldiimidazole, diphenylphosphoryl azide, diethylphosphoryl cyanide, and 1-ethyl-3-(3-dimethylaminopropyl)carbodiimide hydrochloride.

The reaction varies depending on the reactive derivative and the condensing agent to be used but is usually carried out in an organic solvent that is inert to the reaction, such as halogenated hydrocarbons such as dichloromethane, dichloroethane, and chloroform, aromatic hydrocarbons such as benzene, toluene, xylene, ethers such as ether and tetrahydrofuran, esters such as ethyl acetate, acetonitrile, N,N-dimethylformamide, and dimethyl sulfoxide, under cooling, or at a temperature of from cooling temperature to room temperature, or at a temperature of from room temperature to an elevated temperature.

Incidentally, in some case, it is advantageous for making the reaction proceed smoothly that the reaction is carried out by using an excessive amount of the compound (II) or in the presence of a base such as N-methylmorpholine, trimethylamine, triethylamine, N,N-dimethylaniline, pyridine, 4-(N,N-dimethylamino)pyridine, picoline, and lutidine. Further, a salt comprising a weak base and a strong acid, such as pyridine hydrochloride, pyridine p-toluenesulfonate, and N,N-dimethylaniline hydrochloride, may be used. In the case, the imidazole ring fused with the benzazepine forms a slat together with the strong acid, and the liberated weak base functions as a catalyst. Pyridine may be used as the solvent.

Especially, it is suitable to carry out the reaction in a solvent such as acetonitrile and N,N-dimethylformamide in the presence of a base such as pyridine and N,N-dimethylaniline or a salt such as pyridine hydrochloride.

(Second Production Process)

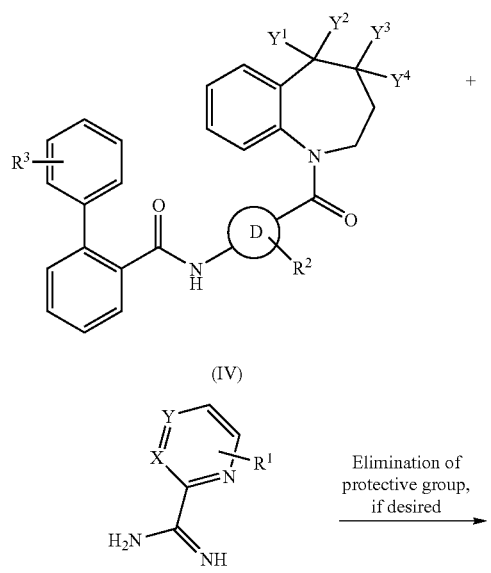

(IV)

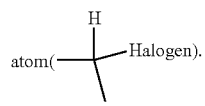

(V) or its salt

Elimination of protective group, if desired
→

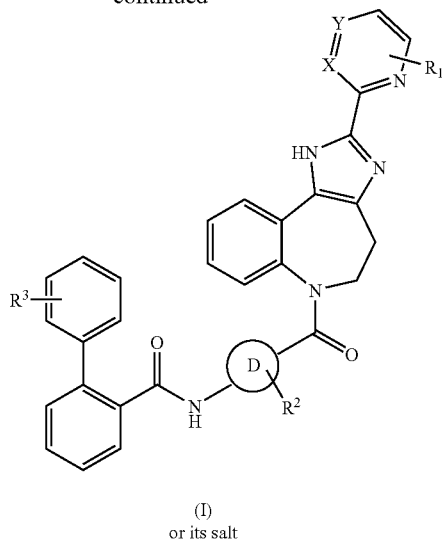

(I)
or its salt (In the formulae, one party of $Y^1$ and $Y^2$, and $Y^3$ and $Y^4$ represents an oxo group (=O), and the other groups represent a halogen atom and a hydrogen atom(—|—Halogen).

The production process is a process in which an optionally protected haloketone represented by the formula (IV) and an optionally protected amidine represented by the formula (V) or its salt are cyclized in an ordinary manner, and the protective group(s) is removed, if desired, to produce the compound (I) of the invention.

In this reaction, in some case, the corresponding amidine forms a salt together with an acid. Further, in order to promote the reaction, the reaction may be carried out in the presence of an inorganic base such as sodium hydroxide, potassium hydroxide, sodium carbonate, potassium carbonate, sodium hydrogencarbonate, and potassium hydrogencarbonate, a salt of a weak base and a strong acid, or an organic base such as pyridine, diisopropylethylamine, and 1,5-diazabicyclo[4.3.0]non-5-ene. As the solvent to be used for the reaction, are preferable solvents that are inert to the reaction, such as alcohols such as methanol, ethanol, and 2-propanol, ethers such as ether, tetrahydrofuran, and dioxane, halogenated hydrocarbons such as dichloromethane, chloroform, and carbon tetrachloride, acetonitrile, dimethylformamide, and dimethyl sulfoxide. The reaction temperature is preferably from room temperature to a refluxing temperature of the solvent. If desired, the reaction is carried out under an elevated pressure.

Incidentally, in this reaction, an oxazole may possibly be formed. In this case, when the reaction is carried out under the condition of adding ammonium carbonate, ammonium acetate, a formamide, etc. in an ammonia gas stream, the imidazole can be given as a main product.

The starting compound (IV) that is used for this reaction can be produced by amidating an optionally protected aromatic carboxylic acid (VI) or its reactive derivative and an optionally protected benzazepine derivative (VII) or its salt in the same manner as in the first production process and then exerting a halogenating agent, as shown in the following reaction scheme (if desired, the protective group(s) is removed at an arbitrary stage). Incidentally, the aromatic carboxylic acid (VI) can be produced by amidating a corresponding, optionally protected 2-phenylbenzoic acid (IX) or its reactive derivative and a corresponding, optionally protected amino aromatic carboxylic acid (X) or its salt in the same manner as in the first production process.

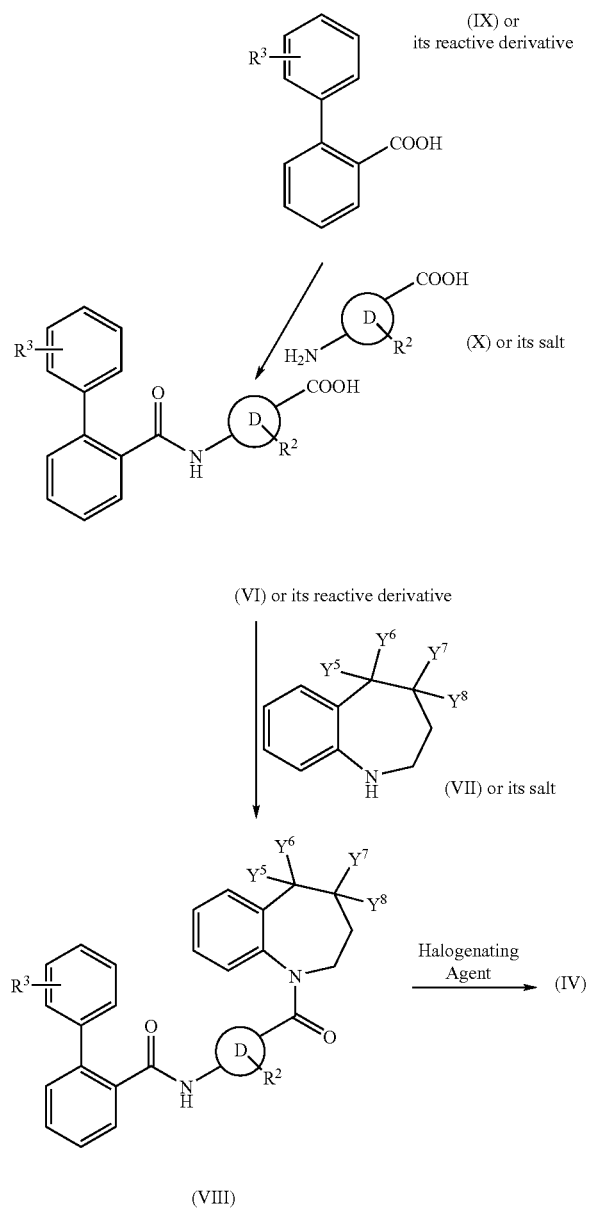

(In the formulae, one party of $Y^5$ and $Y^6$, and $Y^7$ and $Y^8$ represents an oxo group (=O), and the other party each represents a hydrogen atom

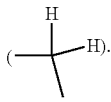

With respect to the first half amidation, the kind of the reactive derivative and the reaction condition are identical with those of the first production process.

As the halogenating agent that is used in the halogenation step, any halogenating agents that are usually used for halogenation of saturated cyclic ketones can be used. Suitable examples include metal reagents such as copper(II) halides such as copper(II) bromide and copper(II) chloride; and perbromides of pyridine, α-pyrrolidone, quaternary ammonium, dioxane, etc., such as dioxane dibromide, phenyltrimethylammonium tribromide, pyridium hydrobromide perbromide, and pyrrolidone hydrotribromide. Further, single halogen such as chlorine and bromine, or hydrogen halides such as hydrogen chloride and hydrogen bromide can also be used.

In the reaction using the metal reagent or perbromide, it is usually advantageous to react the compound (VIII) with the halogenating agent in an organic solvent that is inert to the reaction, such as halogenated hydrocarbons such as dichloromethane, chloroform, and carbon tetrachloride, ethers such as ether, tetrahydrofuran, and dioxane, alcohols such as methanol, ethanol, and 2-propanol, aromatic hydrocarbons such as benzene, toluene, and xylene, acetic acid, and ethyl acetate, or in water, or in a mixed solvent thereof and in the optional presence of a small amount of a catalyst such as hydrogen halides at a temperature of from room temperature to an elevated temperature.

Further, the desired compound can be obtained by reacting the compound (VIII) with a single halogen as the halogenating agent in a solvent that is inert to the reaction, such as halogenated hydrocarbons such as dichloromethane, chloroform, and carbon tetrachloride, ethylene glycol, and acetic acid, or by reacting the compound (VIII) with a hydrogen halide as the halogenating agent in an acidic solution or a basic solution (such as a sodium hydroxide solution). At this time, the reaction temperature is preferably from –30° C. to the refluxing temperature of the solvent to be used.

The thus produced compound of the invention is isolated and purified as a free form or as a salt after subjecting to salt formation in an ordinary manner. The isolation and purification are carried out by applying a usual chemical operation such as extraction, concentration, distillation, crystallization, filtration, recrystallization, and various kinds of chromatography.

Various isomers can be isolated in an ordinary manner by utilizing a difference in physicochemical properties among the isomers. For example, in the case of racemic mixtures, the racemic compound can be introduced into an optically pure isomer by a general racemic resolution method such as a method in which the racemic compound is introduced into a diastereomer salt with a general optically active acid such as tartaric acid, which is then subjected to optical resolution. Further, the mixture of diastereomers can be separated by fractional crystallization or various kinds of chromatography. Moreover, it is possible to produce optically active compounds by using a proper optically active starting material.

INDUSTRIAL APPLICABILITY

The compound of the invention and its salt have a superior antagonism against arginine vasopressin $V_{1A}$ and $V_2$ receptors.

Accordingly, the compound of the invention has actions of profile based on such actions, such as water diuresis action, urine eliminating action, factor VIII secretion inhibiting action, vasodilation action, cardiac function acceleration action, mesangial cell contraction inhibiting action, mesangial cell proliferation inhibiting action, hepatic gluconeogenesis inhibiting action, platelet aggregation inhibiting action, aldosterone secretion inhibiting action, endoserin production inhibiting action, central buffer action, renin secretion regulating action, memory regulating action, body temperature regulating action, and prostaglandin production regulating action; is useful as a characteristic water diuretic, urine eliminant, vasodilator, depressor, drug for heart failure, drug for renal failure, or anticoagulant; and is effective for prevention and/or therapy of heart failure, hyponatremia, syndrome of inappropriate antidiuretic hormone (SIADH), renal diseases (such as nephrosis, nephritis, diabetic nephropathy, and acute or chronic renal failure), brain edema, ascites, hepatic cirrhosis, etc.

Further, since the compound of the invention and its salt have an extremely low inhibition action against the drug metabolizing enzyme CYP3A4, they have a low possibility to cause drug interaction with other drugs to be metabolized through CYP3A4 as compared with known 1,4,5,6-tetrahydroimidazo[4,5-d]benzazepine derivatives. Accordingly, the compound of the invention and its salt are superior from the standpoint that they can be safely used for combined therapy with other drug. Examples of the drugs to be metabolized through CYP3A4 include simvastatin, lovastatin, fluvastatin, atorvastatin, midazolam, nifedipine, amlodipine, and nicardipine (see *SOGORINSHO* (Overall Clinics), 48(6), 1427–1431, 1999).

The pharmacological actions of the compound of the invention were confirmed by the following assays.

(1) $V_{1A}$ Receptor Binding Assay:

A rat hepatic membrane specimen was prepared according to the method of Nakamura, et al. (*Journal of Biological Chemistry*, Vol. 258, No. 15, pp. 9283–9289, 1983). The hepatic membrane specimen (30 μg) was incubated at 25° C. for 60 minutes in a total amount of 250 μL of a 50 mM TRIS-HCl buffer solution (pH: 7.4) containing 10 mM magnesium chloride and 0.1% bovine serum albumin (BSA), together with [$^3$H]-Arg-vasopressin (hereinafter simply referred to as "[$^3$H]-vasopressin") (0.5 nM, specific activity: 75 Ci/mmol) and a test compound (from $10^{-10}$ to $10^{-6}$ M). Thereafter, liberated [$^3$H]-vasopressin and receptor-binding [$^3$H]-vasopressin were separated from each other by using a cell harvester, and the receptor-binding [$^3$H]-vasopressin was adsorbed on a UniFilter plate, GF/B glass filter. After thoroughly drying, the receptor-binding [$^3$H]-vasopressin was mixed with a microplate scintillation cocktail, the amount of the receptor-binding [$^3$H]-vasopressin was measured by using TopCount, and an inhibition rate was calculated according to the following equation.

Inhibition rate (%)=[100−($C_1$−$B_1$)]/($C_0$−$B_1$)×100

$C_1$: An amount of [$^3$H]-vasopressin binding to the membrane specimen when treating the receptor membrane specimen in the co-presence of the test compound having a known concentration and [$^3$H]-vasopressin $C_0$: An amount of [$^3$H]-vasopressin binding to the membrane specimen when treating the receptor membrane specimen in the presence of [$^3$H]-vasopressin and in the absence of the test compound $B_1$: An amount of [$^3$H]-vasopressin binding to the membrane specimen when treating the receptor membrane specimen in the co-presence of [$^3$H]-vasopressin and an excessive amount of vasopressin ($10^{-6}$ M)

According to the foregoing equation, a concentration of the test compound at the inhibition rate of 50% ($IC_{50}$ value) was calculated, from which was then calculated an affinity of the test compound with the receptor, i.e., a dissociation constant (Ki), according to the following equation.

$Ki=IC_{50}/(1+[L]/Kd)$

[L]: A concentration of [$^3$H]-vasopressin

Kd: A dissociation constant of [$^3$H]-vasopressin against the receptor as determined by the saturation binding assay A logarithm of the Ki value as calculated according to the foregoing equation was taken, and its negative value was defined as a pKi value.

(2) $V_2$ Receptor Binding Assay:

A rat renal medullary membrane specimen was prepared according to the method of Cambell, et al. (*Journal of Biological Chemistry*, Vol. 247, No. 19, pp. 6167–6175, 1972). The rat renal medullary membrane specimen (200 μg) was treated together with [$^3$H]-vasopressin (0.5 nM, specific activity: 75 Ci/mmol) and a test compound (from $10^{-10}$ to $10^{-6}$ M) in the same manner as in the foregoing $V_{1A}$ receptor binding assay, and the same measurement was carried out to determine a pKi value.

(3) Cytochrome P450 (3A4) Inhibition Assay:

An assay was carried out according to the method of Crespi, et al. (*Analytical Biochemistry*, 248, 188–190, 1997). Using a 96-well plate, BFC ($5\times10^{-5}$ M) as a substrate, a test compound (from $9.1\times10^{-8}$ to $2\times10^{-5}$ M), and an enzyme ($10^{-8}$ M) were incubated at 37° C. for 30 minutes in a total amount of 100 μL of a 20 mM phosphoric acid buffer solution (pH: 7.4) containing 1.3 mM NADP+, 3.3 mM glucose-6-pharpahte, 3.3 mM magnesium chloride, and 0.4 Units/mL glucose-6-phosphate dehydrogenase. Thereafter, a 100 mM TRIS buffer solution containing 80% acetonitrile was added to stop the reaction, and a fluorescent intensity (excitation wavelength: 409 nm, fluorescent wavelength: 530 nm) was measured by a fluorescent plate reader. An inhibition rate was calculated according to the following equation, and a concentration of the test compound at the inhibition rate of 50% ($IC_{50}$ value) was determined.

Inhibition rate (%)=[100−($C_1$−$B_1$)]/($C_0$−$B_1$)×100

$C_1$: A fluorescent intensity in the presence of the test compound having a known concentration, enzyme and the substrate $C_0$: A fluorescent intensity in the presence of enzyme and the substrate and in the absence of the test compound $B_1$: A fluorescent intensity of the blank well

TABLE 1

Antagonism against arginine vasopressin $V_{1A}$ and $V_2$ receptors and inhibition action against drug metabolizing enzyme CYP3A4

| Example No. | Binding activity against arginine vasopressin $V_{1A}$ receptor (pki) | Binding activity against arginine vasopressin $V_2$ receptor (pKi) | Inhibition activity against drug metabolizing enzyme CYP3A4 ($IC_{50}/\mu M$) |
|---|---|---|---|
| 1 | 8.55 | 8.22 | 7.82 |
| 9 | 8.42 | 7.98 | 2.4 |
| 11 | 8.71 | 7.91 | 2.0 |
| 12 | 8.12 | 7.54 | 5.9 |
| Control compound 1[1] | 8.11 | 8.07 | 0.21 |
| Control compound 2[2] | 8.91 | 8.98 | 0.43 |

[1]N-[4-(2-Benzyl-1,4,5,6-tetrahydroimidazo[4 5-d] [1]benzazepine-6-carbonyl)phenyl]biphenyl-2-carboxamide hydrochloride (a compound of Example 22 as described in WO 95/03305 - but the test compound is a hydrochloride)
[2]N-[4(2-Cyclopropyl-1,4,5,6-tetrahydroimidazo[4,5-d] [1]benzazepine-6-carbonyl)phenyl]biphenyl-2-carboxamide hydrochloride (a compound of Example 23 as described in WO 95/03305 - but the test compound is a hydrochloride)

As shown in Table 1, it has become clear that the compounds of the invention have a superior receptor-binding activity against the $V_{1A}$ receptor and $V_2$ receptor and a low inhibition activity against the drug metabolizing enzyme CYP3A4.

The drug of the invention can be prepared by a usually employed method using one or two or more of the compound of the invention represented by the general formula (I) and a pharmaceutical carrier, excipient and other additives as used for formulation. The administration may be in any form of oral administration by tablets, pills, capsules, granules, powders, liquids, etc., or parenteral administration by injections such as intravenous or intramuscular injection, suppositories, transnasal administration, transmucous administration, dermal administration, etc.

As a solid composition for the oral administration according to the invention, tablets, powders, or granules are used. In such a solid composition, one or more active substances are mixed with at least one inert diluent such as lactose, mannitol, glucose, hydroxypropyl cellulose, microcrystalline cellulose, starch, polyvinylpyrrolidone, and magnesium metasilicate aluminate. The composition may contain additives other than the inert diluent, such as a lubricant such as magnesium stearate, a disintegrating agent such as cellulose calcium glycolate, a stabilizer such as lactose, and a dissolution aid such as glutamic acid and aspartic acid, according to the customary method. If desired, the tablets or pills may be coated by a sugar coating such as sugar, gelatin, hydroxypropyl cellulose, and hydroxypropylmethyl cellulose phthalate, or a film made of a gastric-soluble or intestinal soluble substance.

The liquid composition for oral administration contains a pharmaceutically acceptable emulsion agent, solution agent, suspending agent, syrup, or elixir and contains a generally employed inert diluent such as purified water and ethanol. In addition to the inert diluent, this composition may contain an auxiliary agent such as a wetting agent and a suspending agent, a sweetener, a flavor, an aromatic, or an antiseptic.

The injection for parenteral administration contains a sterile aqueous or non-aqueous solution agent, suspending agent or emulsion agent. Examples of the aqueous solution agent or suspending agent include distilled water or physiological saline for injection. Examples of the non-aqueous solution agent or suspending agent include propylene glycol, polyethylene glycol, vegetable oils such as olive oil, alcohols such as ethanol, and Polysolvate 80. Such a composition may also contain an auxiliary agent such as an antiseptic, a wetting agent, an emulsifier, a dispersing agent, a stabilizer such as lactose, and a dissolution aid such as glutamic acid and aspartic acid. These compositions are sterilized by, for example, filtration through a bacteria-holding filter, compounding with an anti-bacterial agent, or irradiation. Further, these can be used by producing a sterile solid composition and dissolving it in sterile water or a sterile solvent for injection before the use.

Concretely, for example, 1.0 mg of the compound of Example 6, 300 mg of propylene glycol, and 100 mg of ethanol are mixed, to which is then added water for injection to make a total volume of 1 mL, whereby the injection can be prepared.

Usually, in the case of the oral administration, it is proper that the dose of the drug per day is from about 0.0001 to 50 mg per kg, preferably from about 0.001 to 10 mg per kg, and more preferably from 0.01 to 1 mg per kg of the body weight and that the drug is administered once or dividedly two to four times. In the case of the intravenous administration, it is proper that the dose of the drug per day is from about 0.0001 to 1 mg per kg, and preferably from about 0.0001 to 0.1 mg per kg of the body weight and that the drug is administered once or dividedly several times. The dose is properly determined depending on the individuals while taking into consideration the symptom, age and sex.

BEST MODE FOR CARRYING OUT THE INVENTION

The invention will be specifically described below with reference to the following Examples, but it should not be limited thereto. Incidentally, the production processes of the starting compounds to be used in the following Examples will be described with reference to the Referential Examples.

EXAMPLE 1

N-{4-[2-(2-Pyridyl)-1,4,5,6-tetrahydroimidazo[4,5-d][1]benzazepine-6-carbonyl]phenyl}biphenyl-2-carboxamide hydrochloride In 30 mL of tetrahydrofuran was dissolved in 1.0 g of N-[4-(5-oxo-2,3,4,5-tetrahydro-1H-benzazepine-1-carbonyl)phenyl]biphenyl-2-carboxamide, to which was then added 0.902 g of phenyltrimethylammonium tribromide, and the mixture was stirred at room temperature for 150 minutes. An insoluble matter of the reaction mixture was removed by filtration, and the solvent was distilled off in vacuo. The resulting residue was dissolved in 30 mL of chloroform, to which were then added 1.70 g of 2-amidinopyridinium hydrochloride hydrate and 2.1 g of potassium carbonate, and the mixture was refluxed upon heating for 9 hours. The reaction mixture was cooled and rinsed with water, and the chloroform layer was dried over anhydrous magnesium sulfate. The solvent was distilled off, and the resulting residue was subjected to silica gel chromatography and eluted with chloroform-methanol (70:1). To the eluate was added 0.9 mL of a 4M hydrochloric acid-ethyl acetate solution in chloroform, and the solvent was then distilled off. The resulting residue was recrystallized from acetonitrile to obtain 0.830 g of the titled compound.

Compounds of Examples 2 to 4 as shown in Table 2 were produced in the same manner as in Example 1 while using the respective corresponding starting materials.

Incidentally, the abbreviations shown below are used in the table (hereinafter the same).

Ex: Example No., Ref: Referential Example No., salt: salt (no description: free form, HCl: hydrochloride, H$_2$O: hydrate), Data: Physicochemical data, MS: FAB-MS(M+H)$^+$, MS-: FAB-MS(M−H)$^−$, NMR: $^1$H-NMR δ (ppm), m.p.: Melting point (° C.)

REFERENTIAL EXAMPLE 1

2-(2-Pyridyl)-1,4,5,6-tetrahydro-6-(4-methylbenzenesulfonyl)imidazo[4,5-d][1]benzazepine In 30 mL of chloroform was dissolved 2.0 g of 1,2,3,4-tetrahydro-1-(4-methylbenzenesulfonyl)-1-benzazepin-5-one, to which was then added dropwise a solution of 0.33 mL of bromine in 10 mL of chloroform. The mixture was stirred at room temperature for one hour. The reaction mixture was rinsed with saturated sodium hydrogencarbonate and then dried over anhydrous sodium sulfate. The solvent was distilled off, and the resulting residue was dissolved in 30 mL of chloroform. To the solution were added 5.0 g of 2-amidinopyridinium hydrochloride hydrate and 5.3 g of potassium carbonate, and the mixture was refluxed upon heating for 10 hours. The reaction mixture was cooled, and the solvent was then distilled off. To the resulting residue was added 30 mL of a 1M hydrochloric

TABLE 2

| Ex | R | salt | Data |
|---|---|---|---|
| 1 | 2-pyridyl | HCl | NMR(DMSO-d$_6$); 3.00–3.15(1H,m), 3.21–3.40(2H,m), 4.95–5.10 (1H,m), 6.87(1H,d,J=6.8Hz), 6.99(2H,d,J=7.8Hz), 7.18(1H,t,J=7.8Hz), 7.24–7.57(12H,m), 7.70(1H,dd,J=4.6Hz,7.3Hz), 8.19(1H,dt,J=1.4Hz,7.8Hz), 8.45(1H,d,J=7.3Hz), 8.81(1H,d,J=7.8Hz), 8.86(1H,d,J=4.6Hz), 10.31(1H,s). MS; 562. |
| 2 | pyrazinyl | HCl | NMR(DMSO-d$_6$); 2.98–3.10(1H,m), 3.12–3.34(2H,m), 4.93–5.08 (1H,m), 6.79(1H,d,J=7.3Hz), 6.92(2H,d,J=8.0HZ), 7.02(1 H,d,J=8.0Hz), 7.23–7.60(12H,m), 8.33(1H,d,J=8.0Hz), 8.75(1H,d,J=2.2 Hz), 8.77–8.81(1H,m), 9.56(1H,s), 10.28(1H,s). MS; 563. |
| 3 | 3-Me-2-pyridyl | HCl | NMR(DMSO-d$_6$); 2.66(3H,s), 3.00–3.15(1H,m), 3.20–3.37(2H, m), 4.95–5.10(1H,m), 6.85(1H,d,J=7.3Hz), 6.97(2H,d,J=8.1Hz), 7.15(1H,t,J=8.1Hz), 7.25–7.58(13H,m), 8.04(1H,t,J=8.1Hz), 8.37 (1H,d,J=8.1Hz), 8.47(1H,d,J=7.3Hz), 10.29(1H,s). MS-; 574. |
| 4 | pyrimidinyl | HCl | NMR(DMSO-d$_6$); 3.00–3.12(1H,m), 3.15–3.36(2H,m), 4.95–5.06 (1H,m), 6.83(1H,d,J=7.3Hz), 6.95(2H,d,J=7.3Hz), 7.12(1H,t,J=7.3Hz), 7.24–7.56(12H,m), 7.70(1H,t,J=5.1Hz), 8.29(1H,dd,J=1.4 Hz, 8.1Hz), 9.08(2H,d,J=5.1Hz), 10.29(1H,s). MS; 563. | acid aqueous solution, and a deposited solid was collected by filtration. The resulting solid was suspended in chloroform and rinsed with a 1M sodium hydroxide aqueous solution, and the chloroform layer was dried over anhydrous magnesium sulfate. The solvent was distilled off, and the resulting residue was recrystallized from ethanol to obtain 1.70 g of the titled compound.

$^1$H-NMR (DMSO-$d_6$): δ2.12 (3H, s), 3.00 to 3.33 (4H, br), 7.13 (2H, d, J=8.1 Hz), 7.21 (1H, dt, J=1.4 Hz, 8.1 Hz), 7.29 to 7.43 (5H, m), 7.89 (1H, dt, J=1.4 Hz, 8.1 Hz), 8.07 (1H, d, J=8.1 Hz), 8.17 (1H, d, J=7.3 Hz), 8.60 (1H, d, J=4.4 Hz)

REFERENTIAL EXAMPLE 2

2-(2-Pyridyl)-1,4,5,6-tetrahydroimidazo[4,5-d][1]benzazepine

In 9 mL of sulfuric acid and 4.3 mL of acetic acid was dissolved 2.93 g of the compound of Referential Example 1, and the solution was stirred upon heating on a water bath at 70° C. for 90 minutes. The reaction mixture was poured into 100 mL of ice water, to which was then added a 10M sodium hydroxide aqueous solution to make the mixture basic. After further adding 200 mL of methyl ethyl ketone, the mixture was subjected to liquid-liquid separation. The organic layer was rinsed with saturated salt water and then dried over anhydrous sodium sulfate. The solvent was distilled off, and the resulting residue was crystallized from ethyl acetate. A deposited crystal was collected by filtration and dried to obtain 1.038 g of the titled compound.

$^1$H-NMR (DMSO-$d_6$): δ2.97 (2H, t, J=5.1 Hz), 3.20 to 3.26 (2H, m), 5.95 (1H, t, J=3.7 Hz), 6.73 to 6.82 (2H, m), 6.93 (1H, dt, J=1.5 Hz, 7.3 Hz), 7.34 (1H, dd, J=4.4 Hz, 8.1 Hz), 7.86 (1H, dt, J=1.5 Hz, 8.1 Hz), 8.11 (1H, d, J=8.1 Hz), 8.24 (1H, dd, J=1.5 Hz, 8.1 Hz), 8.59 (1H, d, J=4.4 Hz), 12.67 (1H, s)

REFERENTIAL EXAMPLE 3

Methyl 4-[(biphenyl-2-carbonyl)amino]-2-fluorobenzoate

To a solution of 0.66 g of 2-phenylbenzoic acid, 7 mL of tetrahydrofuran, and one drop of N,N-dimethylformamide was added 0.29 mL of thionyl chloride under ice cooling, and the reaction mixture was stirred at room temperature for 2 hours. The reaction mixture was concentrated in vacuo, 3 mL of toluene was added to the residue, and the mixture was again concentrated in vacuo. The resulting residue was dissolved in 3 mL of chloroform, and the solution was added dropwise to a chloroform solution (6 mL) containing 0.56 g of methyl 4-amino-2-fluorobenzoate and 0.63 mL of dimethylaniline under ice cooling. The mixture was stirred at room temperature for 4 hours. The reaction mixture was diluted with ethyl acetate, and the organic layer was rinsed with a 1M hydrochloric acid aqueous solution and a 1M sodium hydroxide aqueous solution. The organic layer was dried over anhydrous sodium sulfate, and the solvent was then distilled off in vacuo. The resulting residue was subjected to silica gel chromatography and eluted with hexane-thyl acetate (3:1) to obtain 1.00 g of the titled compound.

Compounds of Referential Examples 4 to 7 as shown in Table 3 were produced in the same manner as in Referential Example 3 while using the respective corresponding starting materials.

TABLE 3

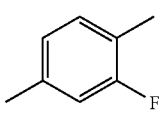

| Ref | R³ | D | R' | Data |
|---|---|---|---|---|
| 3 | H | 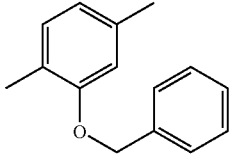 | Me | NMR(CDCl₃); 3.88(3H,s), 6.64(1H,d,J=8.4Hz), 7.01–7.13(1H,m), 7.40–7.61(8H,m), 7.72–7.80(1H,m), 7.87–7.94(1H,m). |
| 4 | H | 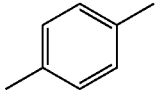 | Me | NMR(CDCl₃); 3.86(3H,s), 7.91(2H,s), 7.18–7.54(13H,m), 7.63–7.68(1H,m), 7.80(1H,dd,J=1.7Hz,7.5Hz), 7.86(1H,s), 8.59(1H,d,J=8.4Hz). |
| 5 | 2-F | | Et | NMR(CDCl₃); 1.37(3H,t,J=7.1Hz), 4.33(2H,q,J=7.1 Hz), 7.11(1H,ddd,J=1.1Hz,8.0Hz,9.5Hz), 7.22(1H, dd,J=1.1Hz,7.5Hz), 7.28–7.45(5H,m), 7.52–7.58(2H,m) (2H,m),7.86(1H,dd,J=1.5Hz,7.7Hz), 7.90–7.95(2H,m). |

TABLE 3-continued

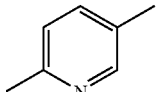

| Ref | R³ | D | R' | Data |
|---|---|---|---|---|
| 6 | H | 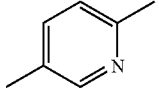 | Me | NMR(CDCl₃); 3.90(3H,s), 6.81(1H,d,J=7.9Hz), 7.05–7.13(1H,m), 7.18–7.59(4H,m), 7.83(1H,m),8.21(1H, ddd,J=2.0Hz,8.8Hz,11.2Hz), 8.25–8.33(2H,m), 8.64–8.67(1H,m), 8.77(1H,d,J=2.0Hz). |
| 7 | H | 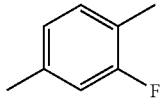 | Me | NMR(CDCl₃); 3.95(3H,s), 7.24–7.71(9H,m), 7.88–7.94 (1H,m), 8.04(1H,d,J=8.6Hz), 8.53–8.58(1H,m). |

REFERENTIAL EXAMPLE 8

4-[(Biphenyl-2-carbonyl)amino]-2-fluorobenzoic acid

In 10 mL of ethanol was dissolved 1.00 g of the compound of Referential Example 3, to which was then added 4.35 mL of a 1M sodium hydroxide aqueous solution. The reaction mixture was stirred at room temperature for 2 days. A 1M hydrochloric acid aqueous solution was added to the reaction mixture to make it have a pH of 6, and a deposited solid was collected by filtration. The resulting solid was recrystallized from ethyl acetate to obtain 0.77 g of the titled compound.

Compounds of Referential Examples 9 to 12 as shown in Table 4 were produced in the same manner as in Referential Example 8 while using the respective corresponding starting materials.

TABLE 4

| Ref | R³ | D | Data |
|---|---|---|---|
| 8 | H | 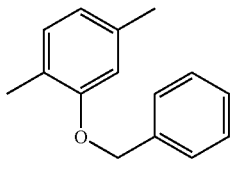 | m.p.:233–235° C. |
| 9 | H | 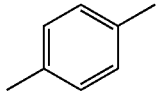 | m.p.:162–164° C. |
| 10 | 2-F | 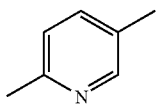 | m.p.:219–222° C. |
| 11 | H | 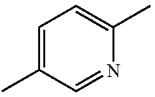 | m.p.:86–89° C. |

TABLE 4-continued

| Ref | R³ | D | Data |
|---|---|---|---|
| 12 | H | 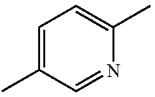 | m.p.113–116° C. |

EXAMPLE 5

N-{4-[2-(2-Pyridyl)-1,4,5,6-tetrahydroimidazo[4,5-d][1]benzazepine-6-carbonyl]phenyl}biphenyl-2-carboxamide monohydrate To a suspension of 3.60 g of 4-[(biphenyl-2-carbonyl)amino]benzoic acid, 100 mL of tetrahydrofuran, and one drop of N,N-dimethylformamide was added 1.21 mL of thionyl chloride under ice cooling, and the reaction mixture was stirred at room temperature for 2 hours 30 minutes. The reaction mixture was concentrated in vacuo, 5 mL of toluene was added to the residue, and the mixture was again concentrated in vacuo. To the resulting residue was added an acetonitrile solution (90 mL) of 2.84 g of the compound of Referential Example 2, and the mixture was stirred upon heating on a water bath at 80° C. for 17 hours 30 minutes. The reaction mixture was cooled to room temperature, and a deposited precipitate was collected by filtration and rinsed with acetonitrile. The resulting solid was suspended in a 1M sodium hydroxide aqueous solution and then extracted with chloroform. The chloroform layer was dried over anhydrous sodium sulfate, and the solvent was distilled off in vacuo. The resulting residue was crystallized from ethyl acetate to obtain 4.921 g of the titled compound.

¹H-NMR (DMSO-d₆): δ2.61 to 3.30 (3H, m), 4.93 to 5.40 (1H, m), 6.72 (1H, d, J=7.3 Hz), 6.88 (2H, d, J=7.8 Hz), 6.96 (1H, t, J=7.8 Hz), 7.24 to 7.56 (13H, m), 7.94 (1H, dt, J=2.0 Hz, 7.8 Hz), 8.19 (1H, d, J=7.8 Hz), 8.29 (1H, d, J=7.3 Hz), 8.65 (1H, d, J=4.4 Hz), 10.28 (1H, s), 13.05 (1H, s) FAB-MS(M+H)⁺: 562 Elemental analysis as C$_{36}$H$_{27}$N$_5$O$_2$.H$_2$O: (Calculated): C: 74.59%, H: 5.04%, N: 12.08%, O: 8.28% (Found): C: 74.89%, H: 5.01%, N: 12.15%

EXAMPLE 6

N-{4-[2-(2-Pyridyl)-1,4,5,6-tetrahydroimidazo[4,5-d][1] benzazepine-6-carbonyl]phenyl}biphenyl-2-carboxamide To 1.0 g of the compound of Example 5 was added 20 mL of acetonitrile, and the mixture was stirred upon heating on an oil bath at 95° C. for 35 minutes. The suspension was cooled to room temperature, and a precipitate was collected by filtration and rinsed with 6 mL of acetonitrile to obtain 0.85 g of the titled compound.

¹H-NMR (DMSO-d$_6$): δ2.97 to 3.26 (3H, m), 4.97 to 5.00 (1H, m), 6.71 (1H, d, J=7.6 Hz), 6.88 (2H, d, J=8.4 Hz), 6.95 (1H, t, J=7.6 Hz), 7.24 to 7.57 (13H, m), 7.94 (1H, dt, J=1.6 Hz, 7.6 Hz), 8.18 (1H, d, J=7.6 Hz), 8.30 (1H, d, J=8.0 Hz), 8.63 (1H, d, J=4.8 Hz), 10.27 (1H, s), 13.03 (1H, s) FAB-MS(M+H)⁺: 562 Melting point: 240 to 242° C. Elemental analysis as C$_{36}$H$_{27}$N$_5$O$_2$ (Calculated): C: 76.99%, H: 4.85%, N: 12.47%, O: 5.70% (Found): C: 77.08%, H: 4.93%, N: 12.39%

EXAMPLE 7

N-{4-[2-(2-Pyridyl)-1,4,5,6-tetrahydroimidazo[4,5-d][1] benzazepine-6-carbonyl]phenyl}biphenyl-2-carboxamide hydrochloride To a suspension of 0.605 g of 4-[(biphenyl-2-carbonyl) amino]benzoic acid, 10 mL of tetrahydrofuran, and one drop of N,N-dimethylformamide was added 0.167 mL of ice-cooled thionly chloride, and the reaction mixture was stirred at room temperature for 4 hours. The reaction mixture was concentrated in vacuo, 5 mL of toluene was added to the residue, and the mixture was again concentrated in vacuo. To the resulting residue was added an acetonitrile solution (25 mL) of 0.385 g of the compound of Referential Example 2, and the mixture was stirred upon heating on a water bath at 80° C. for 4 hours. The reaction mixture was cooled to room temperature, and a deposited precipitate was collected by filtration and rinsed with acetonitrile. The resulting solid was suspended in a 1M sodium hydroxide aqueous solution and extracted with chloroform. The chloroform layer was dried over anhydrous sodium sulfate, and the solvent was distilled off in vacuo. The resulting residue was subjected to silica gel column chromatography and eluted with chloroform-methanol (49:1). The eluate was concentrated in vacuo, and the resulting residue was crystallized from ethyl acetate to obtain 0.566 g of N-{4-[2-(2-pyridyl)-1,4,5,6-tetrahydroimidazo[4,5-d][1]benzazepine-6-carbonyl] phenyl}biphenyl-2-carboxamide. The resulting crystal was suspended in an ethyl acetate-methanol mixed solution, to which was then added 0.277 mL of a 4M hydrochloric acid-ethyl acetate solution, and the solvent was distilled off in vacuo. The resulting residue was suspended in 20 mL of ethanol, and the suspension was stirred upon heating on a water bath at 80° C. for 10 minutes. The suspension was cooled to room temperature, and a precipitate was collected by filtration and rinsed with ethanol to obtain 0.350 g of the titled compound.

The physicochemical data of Example 7 were identical with those of Example 1.

Compounds of Examples 8 to 11 and a compound of Referential Example 13 as shown in Table 5 were produced in the same manner as in Example 7 while using the respective corresponding starting materials.

EXAMPLE 12

N-{2-Hydroxy-4-[2-(2-pyridyl)-1,4,5,6-tetrahydroimidazo [4,5-d][1]-benzazepine-6-carbonyl]phenyl}biphenyl-2-carboxamide hydrochloride In 6 mL of trilfuoroacetic acid was dissolved 0.525 g of the compound of Referential Example 13, to which was then added 0.466 g of pentamethylbenzne. The reaction mixture was stirred at room temperature for 3 hours, and 0.233 g of pentamethylbenzene was further added to the reaction mixture. The reaction mixture was stirred at room temperature for an additional 21 hours. The reaction mixture was concentrated in vacuo, 3 mL of toluene was added to the residue, and the mixture was again concentrated in vacuo. The resulting residue was dissolved in 10 mL of chloroform, to which was then added 10 mL of a 1M sodium hydroxide aqueous solution, and a deposited solid was collected by filtration. To the resulting solid was added 0.20 mL of a 4M hydrochloric acid-ethyl acetate solution, and the solvent was distilled off. The resulting residue was recrystallized from ethanol to obtain 0.300 g of the titled compound.

TABLE 5

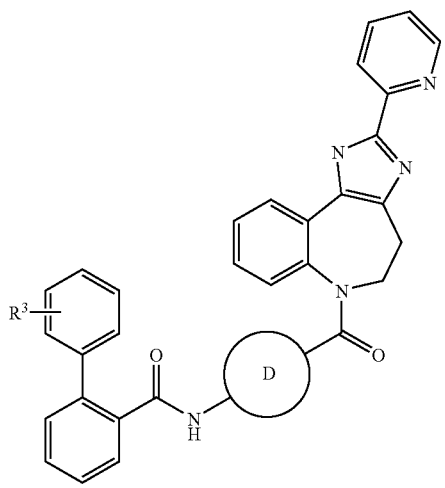

|  | R³ | D | salt | Data |
|---|---|---|---|---|
| Ex 8 | H | 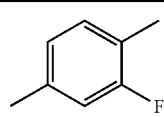 | HCl | NMR(DMSO-d₆); 3.08–3.28(2H,m), 3.30–3.42(1H, m), 4.88–4.98(1H,m), 6.92(1H,d,J=8.1Hz), 7.08–7.18(2H,m), 7.25(1H,d,J=8.0Hz), 7.28–7.40(7H, m), 7.47(2H,t,J=8.1Hz), 7.54–7.60(2H,m), 7.63–7.68 (1H,m), 8.15(1H,t,J=6.6Hz), 8.33(1H,d,J=8.0Hz), 8.60(1H,d,J=7.3Hz), 8.82(1H,d,J=4.4Hz), 10.45 (1H,s). MS; 580. |
| Ex 9 | 2-F | 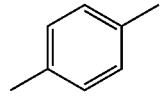 | HCl | NMR(DMSO-d₆); 2.97–3.14(1H,m), 3.18–3.40(2H, m), 4.90–5.11(1H,m), 6.86(1H,d,J=7.3Hz), 6.98 (2H,d,J=7.3Hz), 7.10–7.21(3H,m), 7.28–7.43(6H, m), 7.48–7.68(4H,m), 8.16(1H,t,J=7.3Hz), 8.42(1H, d,J=8.1Hz), 8.73(1H,d,J=7.3Hz), 8.83(1H,d,J= 4.4Hz), 10.36(1H,s). MS; 580. |
| Ex 10 | H | 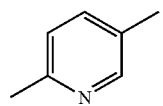 | HCl | NMR(DMSO-d₆); 3.05–3.18(1H,m), 319–3.40(2H, m), 4.93–5.08(1H,m), 6.96(1H,d,J=8.0Hz), 7.19 (1H,t,J=7.4Hz), 7.24–7.57(11H,m), 7.61(1H,dd,J= 7.1Hz,7.3Hz), 7.74–7.82(1H,m), 7.83–7.89(1H, m), 8.15(1H,dt,J=1.6Hz,8.0Hz), 8.40(1H,d,J=8.0 Hz), 8.58–8.68(1H,m), 8.81(1H,d,J=4.4Hz), 10.75 (1H,s). MS; 563. |
| Ex 11 | H | 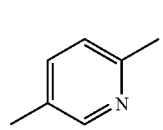 | HCl | NMR(DMSO-d₆); 3.10(1H,dt,J=2.9Hz, 13.2Hz), 3.02–3.40(2H,m), 4.98(1H,dd,J=5.2Hz, 13.2Hz), 6.77(1H,d,J=8.0Hz), 7.09(1H,t,J=7.3Hz), 7.24–7.69 (13H,m), 7.90(1H,dd,J=2.2Hz,8.8Hz), 8.14(1H, t,J=7.3Hz), 8.30(1H,d,J=7.3Hz), 8.56(1H,d,J= 8.1Hz), 8.81(1H,d,J=4.4Hz), 10.47(1H,s). MS; 563. |
| Ref 13 | H | 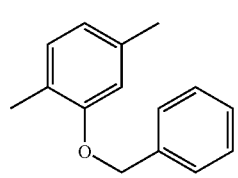 |  | NMR(DMSO-d₆); 2.96–3.20(3H,m), 4.87–4.99 (1H,m), 6.34(1H,brs), 6.65–6.78(2H,m), 6.94–7.02 (1H,m), 7.08–7.50(15H,m), 7.55(1H,t,J=7.0Hz), 7.64–7.71(1H,m), 7.94(1H,dt,J=1.7Hz,7.7Hz), 8.23 (1H,d,J=8.1Hz), 8.31(1H,s), 8.35–8.41(1H,m),8.65–8.72(1H,m), 9.06(1H,brs), 13.06(1H,brs). |
| Ex 12 | H | 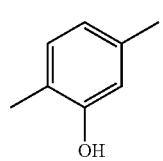 | HCl | NMR(DMSO-d₆); 2.98–3.10(1H,m), 3.17–3.25 (2H,m), 4.90–5.08(1H,m), 6.34(1H,d,J=5.9Hz), 6.76 (1H,s), 6.82–6.90(1H,m), 7.15(1H,t,J=7.3Hz), 7.26–7.49(8H,m), 7.53–7.59(2H,m), 7.65(1H,dd,J=5.1 Hz,7.3Hz), 8.15(1H,t,J=8.8Hz), 8.50(1H,d,J=8.1 Hz), 8.75–8.85(2H,m), 9.13(1H,s), 10.00(1H,s). MS; 578. |

Structures of other compounds of the invention will be shown in Tables 6 to 8. These compounds can be easily synthesized in the foregoing production processes or the processes as described in the Examples, or by undergoing slight modifications within the range obvious to those skilled in the art.

Incidentally, the term "No" in the tables means a compound number.

TABLE 6

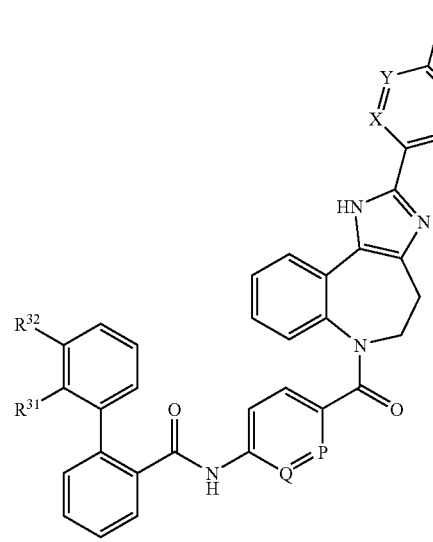

| No | X | Y | R11 | R12 | P | Q | R31 | R32 |
|---|---|---|---|---|---|---|---|---|
| A1 | CH | N | H | H | CH | CH | F | H |
| A2 | CH | N | H | H | CF | CH | H | H |
| A3 | CH | N | H | H | N | CH | H | H |
| A4 | CH | N | H | H | CH | N | H | H |
| A5 | CH | N | H | H | CH | C(OH) | H | H |
| A6 | N | CH | H | H | CH | CH | F | H |
| A7 | N | CH | H | H | CF | CH | H | H |
| A8 | N | CH | H | H | N | CH | H | H |
| A9 | N | CH | H | H | CH | N | H | H |
| A10 | N | CH | H | H | CH | C(OH) | H | H |
| A11 | CH | CH | CH3 | H | CH | CH | F | H |
| A12 | CH | CH | CH3 | H | CF | CH | H | H |
| A13 | CH | CH | CH3 | H | N | CH | H | H |
| A14 | CH | CH | CH3 | H | CH | N | H | H |
| A15 | CH | CH | CH3 | H | CH | C(OH) | H | H |
| A16 | CH | CH | H | H | CH | CH | Cl | H |
| A17 | CH | CH | H | H | CH | CH | H | Cl |
| A18 | CH | CH | H | H | CH | CH | OH | H |
| A19 | CH | CH | H | H | CH | CH | H | OH |
| A20 | CH | CH | Cl | H | CH | CH | H | H |
| A21 | CH | CH | H | CH3 | CH | CH | H | H |

TABLE 7

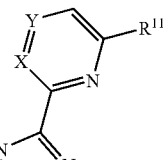

| No. | X | Y | R11 | P | Q | R | T | R31 |
|---|---|---|---|---|---|---|---|---|
| A22 | CH | CH | H | CH | CH | CH | CH | F |
| A23 | CH | CH | H | CH | CH | CH | CH | H |
| A24 | CH | CH | H | N | CH | CH | CH | H |
| A25 | CH | CH | H | CH | N | CH | CH | H |
| A26 | CH | CH | H | CH | CH | N | CH | H |
| A27 | CH | CH | H | CH | CH | CH | N | H |
| A28 | CH | CH | H | CF | CH | CH | CH | H |
| A29 | N | CH | H | CH | CH | CH | CH | H |
| A30 | CH | N | H | CH | CH | CH | CH | H |
| A31 | CH | CH | CH3 | CH | CH | CH | CH | H |

TABLE 8

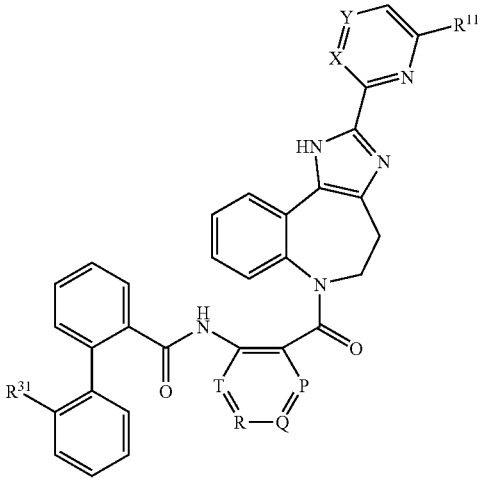

| No | X | Y | R11 | P | Q | R | T | R31 |
|---|---|---|---|---|---|---|---|---|
| A32 | CH | CH | H | CH | CH | CH | CH | F |
| A33 | CH | CH | H | CH | CH | CH | CH | H |
| A34 | CH | CH | H | N | CH | CH | CH | H |
| A35 | CH | CH | H | CH | N | CH | CH | H |
| A36 | CH | CH | H | CH | CH | N | CH | H |
| A37 | CH | CH | H | CH | CH | CH | N | H |
| A38 | CH | CH | H | CF | CH | CH | CH | H |
| A39 | N | CH | H | CH | CH | CH | CH | H |
| A40 | CH | N | H | CH | CH | CH | CH | H |
| A41 | CH | CH | CH3 | CH | CH | CH | CH | H |

The invention claimed is:

1. A compound of formula (I) or a pharmaceutically acceptable salt thereof:

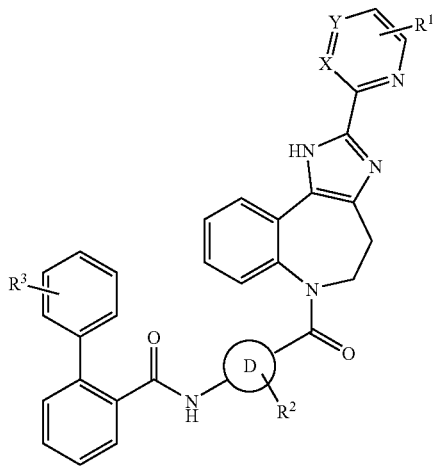

wherein the ring D represents phenylene or pyridinediyl; X and Y may be the same or different and each represents CH or N; and $R^1$, $R^2$ and $R^3$ may be the same or different and each represents a hydrogen atom, a hydroxyl group, a halogen, or a lower alkyl.

2. The compound or its pharmaceutically acceptable salt according to claim 1, wherein the ring D represents 1,4-phenylene, pyridine-2,5-diyl, or pyridine-3,6-diyl.

3. The compound or its pharmaceutically acceptable salt according to claim 2, wherein X and Y each represents OH, and $R^1$ represents a hydrogen atom.

4. The compound or its pharmaceutically acceptable salt according to claim 3, wherein the ring D represents 1,4-phenylene, and $R^2$ and $R^3$ each represents a hydrogen atom.

5. The compound or its pharmaceutically acceptable salt according to claim 1, wherein the compound is
N-{4-[2-(2-pyridyl)-1,4,5,6-tetrahydroimidazo[4,5-d][1]benzazepine-6-carbonyl]phenyl}biphenyl-2-carboxamide,
N-{3-fluoro-4-[2-(2-pyridyl)-1,4,5,6-tetrahydroimidazo[4,5-d][1]benzazepine-6-carbonyl]phenyl}biphenyl-2-carboxamide,
2'-fluoro-N-{4-[2-(2-pyridyl)-1,4,5,6-tetrahydroimidazo[4,5-d][1]benzazepine-6-carbonyl]phenyl}biphenyl-2-carboxamide,
N-{5-[2-(2-pyridyl)-1,4,5,6-tetrahydroimidazo[4,5-d][1]benzazepine-6-carbonyl]-2-pyridyl}biphenyl-2-carboxamide,
N-{6-[2-(2-pyridyl)-1,4,5,6-tetrahydroimidazo[4,5-d][1]benzazepine-6-carbonyl]-3-pyridyl}biphenyl-2-carboxamide, or
N-{2-hydroxy-4-[2-(2-pyridyl)-1,4,5,6-tetrahydroimidazo[4,5-d][1]benzazepine-6-carbonyl]phenyl}biphenyl-2-carboxamide.

6. A composition comprising the compound or its pharmaceutically acceptable salt according to any one of claims 1 to 5, and a pharmaceutical carrier or excipient.

7. A composition comprising a compound or its pharmaceutically acceptable salt, and a pharmaceutical carrier or excipient, wherein the compound is
N-{4-[2-(2-pyridyl)-1,4,5,6-tetrahydroimidazo[4,5-d][1]benzazepine-6-carbonyl]phenyl}biphenyl-2-carboxamide,
N-{3-fluoro-4-[2-(2-pyridyl)-1,4,5,6-tetrahydroimidazo[4,5-d][1]benzazepine-6-carbonyl]phenyl}biphenyl-2-carboxamide,
2'-fluoro-N-{4-[2-(2-pyridyl)-1,4,5,6-tetrahydroimidazo[4,5-d][1]benzazepine-6-carbonyl]phenyl}biphenyl-2-carboxamide,
N-{5-[2-(2-pyridyl)-1,4,5,6-tetrahydroimidazo[4,5-d][1]benzazepine-6-carbonyl]-2-pyridyl}biphenyl-2-carboxamide,
N-{6-[2-(2-pyridyl)-1,4,5,6-tetrahydroimidazo[4,5-d][1]benzazepine-6-carbonyl]-3-pyridyl}biphenyl-2-carboxamide, or
N-{2-hydroxy-4-[2-(2-pyridyl)-1,4,5,6-tetrahydroimidazo[4,5-d][1]benzazepine-6-carbonyl]phenyl}biphenyl-2-carboxamide.

* * * * *

UNITED STATES PATENT AND TRADEMARK OFFICE
CERTIFICATE OF CORRECTION

| | | |
|---|---|---|
| PATENT NO. | : 7,056,910 B2 | Page 1 of 1 |
| APPLICATION NO. | : 10/432732 | |
| DATED | : June 6, 2006 | |
| INVENTOR(S) | : Hiroyuki Koshio et al. | |

It is certified that error appears in the above-identified patent and that said Letters Patent is hereby corrected as shown below:

On the title page, item (54), lines 1-2, "1,4,5.6-TETRAHYDROIMIDAZO[4,5-D] DIAZEPINE" should read --1,4,5,6-TETRAHYDROIMIDAZO[4,5-D]DIAZEPINE--.

In claim 3, column 27, line 35, "OH," should read --CH,--.

Signed and Sealed this

Seventeenth Day of October, 2006

JON W. DUDAS
*Director of the United States Patent and Trademark Office*